US012728033B2

(12) United States Patent
Cerame

(10) Patent No.: US 12,728,033 B2
(45) Date of Patent: Sep. 8, 2026

(54) THERMAL COMPRESSIVE SURGICAL TREATMENT MASK

(71) Applicant: Mario A. Cerame, Bluffton, SC (US)

(72) Inventor: Mario A. Cerame, Bluffton, SC (US)

( * ) Notice: Subject to any disclaimer, the term of this patent is extended or adjusted under 35 U.S.C. 154(b) by 0 days.

(21) Appl. No.: 19/174,622

(22) Filed: Apr. 9, 2025

(65) Prior Publication Data

US 2025/0312188 A1 Oct. 9, 2025

Related U.S. Application Data

(60) Provisional application No. 63/631,683, filed on Apr. 9, 2024.

(51) Int. Cl.
*A61F 7/02* (2006.01)
*A61F 7/00* (2006.01)

(52) U.S. Cl.
CPC ........ *A61F 7/02* (2013.01); *A61F 2007/0003* (2013.01); *A61F 2007/0219* (2013.01); *A61F 2007/0228* (2013.01); *A61F 2007/0244* (2013.01); *A61F 2007/0282* (2013.01)

(58) Field of Classification Search
CPC ................ A61F 7/02; A61F 2007/0003; A61F 2007/0219; A61F 2007/0228; A61F 2007/0244; A61F 2007/0282
See application file for complete search history.

(56) References Cited

U.S. PATENT DOCUMENTS

| | | | | |
|---|---|---|---|---|
| 4,189,141 A * | 2/1980 | Rooney | A63B 23/03 | 482/11 |
| 4,446,576 A * | 5/1984 | Hisataka | A63B 71/10 | 2/9 |
| 2007/0299489 A1* | 12/2007 | Francis | A41D 31/12 | 607/108 |
| 2011/0036358 A1* | 2/2011 | Mattalino | A61F 13/122 | 607/104 |
| 2011/0196458 A1* | 8/2011 | Bratcher, Jr. | A61F 7/02 | 607/108 |
| 2014/0222121 A1* | 8/2014 | Spence | A61F 7/02 | 607/104 |

(Continued)

*Primary Examiner* — Joseph A Stoklosa
*Assistant Examiner* — Adam J Avigan
(74) *Attorney, Agent, or Firm* — Thompson Patent Law Offices PC

(57) ABSTRACT

Apparatus and associated methods relate to a thermal compressive surgical treatment mask. In an illustrative example, a multi-layered mask assembly is configured to simultaneously apply heat or cold and graduated compression to a predetermined medical target area (e.g., skull cap, face, ears, jaw, chin, or neck). The multi-layered mask assembly includes a multi-layered mask including a silicone-based gel layer and an aperture configured to fit the eyes and nose. A detachable neck strap is operably coupled to the multi-layered mask to extend therapeutic coverage along the cervical region. The multi-layered mask assembly is configured to provide effective thermal therapy and compressive therapy to reduce pain and swelling and enhance lymphatic and venous drainage for a patient post-surgery. Various embodiments may advantageously conform to different anatomical regions, accommodate diverse surgical procedures, and improve patient comfort and recovery by integrating both thermal and compressive functionalities in a single wearable system.

15 Claims, 7 Drawing Sheets

(56) References Cited

U.S. PATENT DOCUMENTS

| | | | | |
|---|---|---|---|---|
| 2016/0051402 | A1* | 2/2016 | Laghi | A61F 13/124<br>607/109 |
| 2018/0042322 | A1* | 2/2018 | Weiler | A41H 3/007 |
| 2018/0344515 | A1* | 12/2018 | Ebben | A41D 19/01541 |
| 2020/0268066 | A1* | 8/2020 | Gonzalez | A41D 1/22 |

* cited by examiner

SILICON GEL THERMAL RETENTIVE PROPERTY

720
°F
70°
60°
50°
40°
30°
20°
70
44
36.5
28
28.5
26
25
24.3
24
34
41
47.5
51.7
55.2
57.9
59.9
61.5
62.6
63.8
705
710
715
TIME
5
10
15
20
25
30
35
40
45

THERMAL COMPRESSIVE SURGICAL TREATMENT MASK

CROSS-REFERENCE TO RELATED APPLICATIONS

This application claims the benefit of U.S. Application Ser. No. 63/631,683, titled "Thermal Compressive Surgical Treatment Mask," filed by Dr. Mario Cerame on Apr. 9, 2024.

TECHNICAL FIELD

Various embodiments relate generally to a surgical post-operative care and medical care.

BACKGROUND

Surgery involves operative interventions to diagnose or treat diseases, injuries, or deformities. It spans from life-saving procedures to elective surgery, which is undertaken by choice for non-life-threatening conditions, often to improve quality of life or aesthetic appeal. Pain management is an integral part of the surgical process, employing various techniques from medication to nerve blocks, ensuring patient comfort and facilitating smoother recovery. Postoperative care also addresses swelling, a common and natural response of the body to surgery, through methods like elevation, compression, and the application of cold, aiming to reduce inflammation and aid in the healing process.

SUMMARY

Apparatus and associated methods relate to a thermal compressive surgical treatment mask. In an illustrative example, a multi-layered mask assembly is configured to simultaneously apply heat or cold and graduated compression to a predetermined medical target area (e.g., skull cap, face, ears, jaw, chin, or neck). The multi-layered mask assembly includes a multi-layered mask including a silicone-based gel layer and an aperture configured to fit the eyes and nose. A detachable neck strap is operably coupled to the multi-layered mask to extend therapeutic coverage along the cervical region. The multi-layered mask assembly is configured to provide effective thermal therapy and compressive therapy to reduce pain and swelling and enhance lymphatic and venous drainage for a patient post-surgery. Various embodiments may advantageously conform to different anatomical regions, accommodate diverse surgical procedures, and improve patient comfort and recovery by integrating both thermal and compressive functionalities in a single wearable system.

Various embodiments may achieve one or more advantages. For example, some embodiments may provide a non-invasive, reusable solution that simultaneously delivers thermal therapy and graduated compression to anatomically complex regions such as the face, jaw, and neck. The silicone-based gel layer may, for example, retain therapeutic temperatures while conforming to patient contours, enhancing both comfort and treatment efficacy. The detachable neck strap may, for example, extend coverage to the cervical region, supporting fluid drainage from the head and minimizing post-surgical edema. Some embodiments may, for example, eliminate the need for separate ice packs or compression wraps by integrating both functions into a unified system. These advantages may, for example, support recovery following cosmetic, reconstructive, dental, thyroid, and lymphatic surgeries by reducing swelling, relieving pain, and promoting efficient lymphatic and venous return through tailored anatomical fit and continuous therapeutic contact.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

To aid understanding, this document is organized as follows. First, to help introduce discussion of various embodiments, an illustrative use-case scenario introduced with reference to FIGS. 1-3. Second, that introduction leads to a description with reference to FIG. 4-7 of some exemplary methods to determine a mask for a user and to use a mask for postoperative surgical care.

Figure 1:
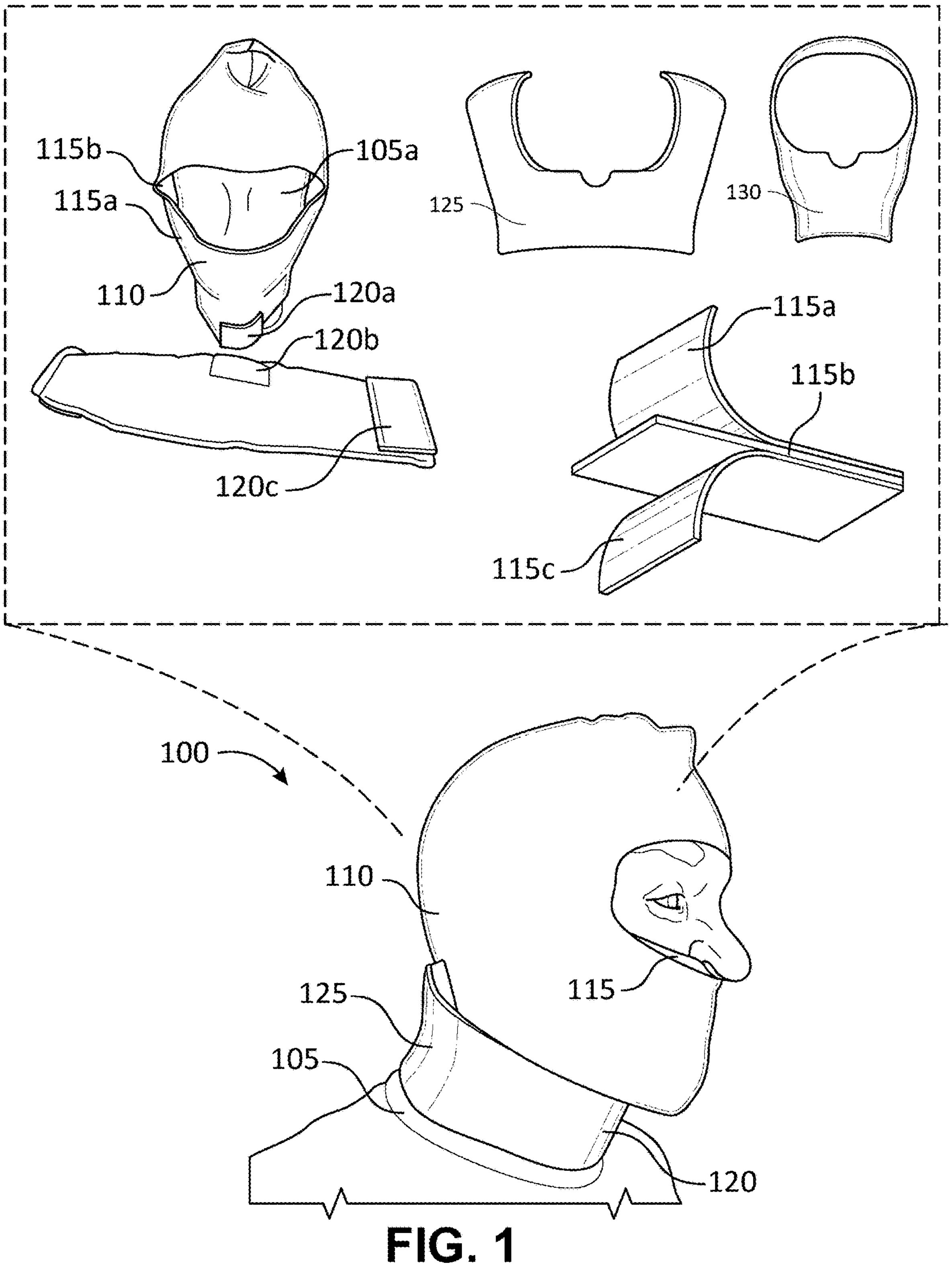
FIG. 1 depicts an exemplary compressive facemask employed in an illustrative use-case scenario.

FIG. 1 depicts an exemplary compressive facemask employed in an illustrative use-case scenario 100. The illustrative use-case scenario 100 includes a user 105. The user is wearing a thermal-compressive surgical-treatment mask 110. The thermal-compressive surgical-treatment mask 110 includes a user aperture 105*a*. The user aperture may, for example, aperture designed for the face and nose, ensuring unobstructed breathing and optimal fit, The aperture may, for example, be designed to maintain the integrity of the therapeutic compression and thermal treatment zones. The potential users of the thermal-compressive surgical-treatment mask may, for example, include patients recovering from surgeries such as lymphadenectomy or cosmetic procedures that affect the facial, jaw, and neck regions. The users may, for example, be seeking to mitigate pain and enhance lymphatic drainage. Users may, for example, want to manage swelling and discomfort post-surgery.

The thermal-compressive surgical-treatment mask 110 includes layers 115. The layers include an exterior fabric 115*a*. The exterior fabric 115*a* may, for example, include a stretchy and resilient fabric. The layers 115 include a silicone gel 115*b*. The layers may include an inner cushioning layer of 115*c*. The inner cushioning layer may, for example, include a comfortable stretchy fabric. The thermal-compressive surgical treatment mask system may, for example, include a neck liner 125. The thermal-compressive surgical treatment mask system may, for example, include a facial liner 130.

In some embodiments, the viscoelastic nature of silicone allows the mask to conform closely to the complex contours of the face, jaw, and neck, providing a snug fit that is both comfortable and effective in delivering targeted pressure and thermal therapy. Silicone gel's low thermal conductivity may, for example, allow the mask to maintain a consistent temperature over time, either retaining warmth or coolness, which is essential for managing swelling and promoting healing post-surgery. The silicone's high thermal stability and durability may, for example, allow the mask to withstand repeated use and cleaning. The inherent flexibility and softness of silicone may, for example, minimize the risk of irritation or discomfort, making it an ideal material for patients with sensitive skin or those requiring long-term wear. The silicone's combination of mechanical and thermal properties may, for example, therapeutic benefits of the mask, contributing to a more efficient and comfortable recovery process.

In some embodiments, incorporating the exterior portion of the thermal-compressive surgical-treatment mask may, for example, amplify the compressive forces for the mask's therapeutic efficacy. The exterior may, for example, be crafted from a resilient and stretchable fabric like neoprene. The exterior may, for example, serve as a protective barrier. The exterior may, for example, serve as a thermal insulator. The exterior may, for example, serve as to contribute to the application of uniform compressive force across the treated area. Compression may, for example, reduce swelling, enhance drainage, and promote blood circulation. These parameters may, for example, aid in the post-surgical healing process.

For example, the exterior's elasticity may, for example, allow the mask to adapt to the contours of the face, jaw, and neck, ensuring that the compression is not only effective but also evenly distributed, minimizing the risk of localized pressure points that could lead to discomfort or compromised circulation. The outer exterior layer may, for example, works in synergy with the mask's overall layered structure, which may include a viscoelastic silicone gel core that conforms to the body's anatomy, thereby enhancing the compressive and thermal therapeutic benefits.

The thermal-compressive surgical-treatment mask 110 includes a neck fastener mechanism 120. The neck fastener device may, for example, be coupled to the exterior layer of the thermal compressive surgical treatment mask by a receiving coupling device 120*a*. The receiving coupling device may, for example, include Velcro. The neck fastener device may, for example, use an opposing coupling device 120*b* that may, for example, couple to the receiving coupling device 120*a*. A user may, for example, couple the neck fastening device to the front of a user's face and use a rear fastening device 120*c* to secure the rear side of the neck fastener device to the compressive mask.

In some embodiments, a thermal-compressive pressure gradient mask may include an aperture configured based on a surgical treatment site, with a method of determining the aperture's location depending on the type and position of the surgery. The mask may be configured as a pain management system wearable on the chin, jaw, neck, and/or head of a patient, delivering thermal therapy via a silicone-based gel with fluidic properties. This gel layer may, for example, conform to diverse anatomical variations in face and skull architecture, improving fit and contact. The aperture may, for example, be dimensioned to avoid interference with the eyes and nose while preserving effective compressive and thermal coverage across the rest of the target region. Aperture positioning may, for example, be customized based on patient-specific treatment zones or post-operative incision locations. The mask may be used in either a clinical or at-home recovery setting.

In some embodiments, the thermal-compressive mask may incorporate graduated compression materials to optimize pressure differentials across various facial regions. These materials may, for example, improve lymphatic and venous drainage, preventing fluid stasis while avoiding ischemia or discomfort. The compression gradient may, for example, be designed to apply higher pressure to regions near the scalp and jawline and lower pressure near sensitive or healing areas. This approach may, for example, help mobilize fluid away from surgical sites and toward natural drainage pathways. The mask may be particularly beneficial for patients recovering from procedures such as lymphadenectomy or plastic surgery flaps, where normal drainage has been disrupted. The compression design may also assist in managing swelling while maintaining comfort during extended wear.

In some embodiments, the system may be configured to provide both thermal application and compressive support, predominantly worn over the face, jaw, and head of a post-surgical patient. Postoperative patients are often instructed to apply ice to reduce swelling, but conventional methods lack integrated compression and are difficult to secure consistently. The described device may, for example, apply a mild to moderate and anatomically conforming pressure while simultaneously delivering cooling or heating to the affected area. This dual-action therapy may, for example, alleviate pain and inflammation more effectively than ice packs or wraps alone. The mask may be reusable and adaptable to different surgical contexts, including cosmetic and dental applications. Its form-fitting nature may enhance therapeutic coverage while eliminating the need for handheld or improvised cooling solutions.

In some embodiments, the thermal-compressive surgical mask may be designed as a pressurized system configured to cover the chin, neck, jaw, ears, and skull cap. The system may, for example, maintain a target temperature by connecting to an external heating or cooling source, or by passive retention of heat or cold within the silicone gel layer. A narrower neck section may help keep the mask positioned below the chin, while a skull cap portion may prevent slippage during use. Posterior seaming may, for example, enable the mask to wrap around the ears, providing therapeutic contact to auricular regions. Embodiments may include stretchable fabrics or neoprene-like materials layered over the silicone for enhanced comfort and flexibility. These features may, for example, support both static rest applications and light ambulatory use during recovery.

Some embodiments may, for example, include an exemplary compressive facemask inner liner. For example, for the cushion liner materials such as soft microfiber fabrics and breathable, moisture-wicking textiles may, for example, be used. The materials may, for example, be chosen based on parameters such as their skin-friendly properties, durability, and ability to provide comfort while conforming to facial contours.

Figure 2A:
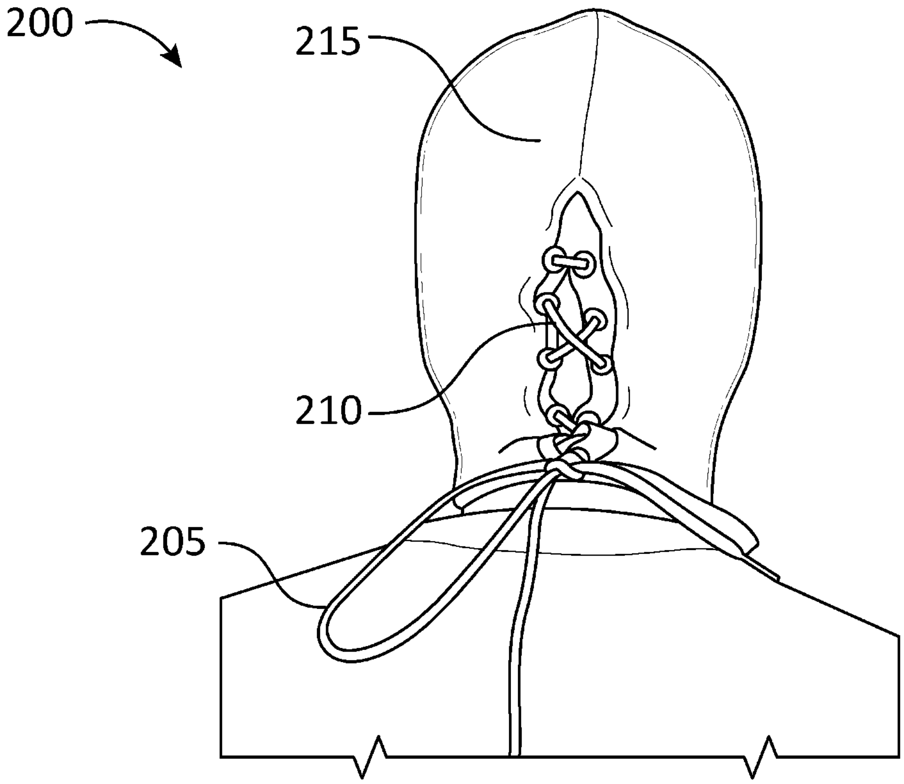
FIG. 2A depicts an exemplary thermal compressive mask lacing embodiment.

FIG. 2A depicts an exemplary thermal compressive mask lacing embodiment 200. The system 200 includes a mask 215 configured to cover a user's cranial and cervical regions. A cord 205 is routed through a plurality of holes 210 disposed along the posterior midline of the mask 215. This opening along the back not only enables tension adjustment for customizable compressive force but also helps avoid some of the shearing forces on the facial flaps during the delicate early postoperative period, enhancing healing and minimizing flap displacement. The lace-tightening system enables the user or caregiver to incrementally adjust tension to conform to anatomical variations while preserving therapeutic contact. This embodiment may be particularly beneficial for post-operative patients requiring adjustable gradient compression across the head and neck.

Figure 2B:
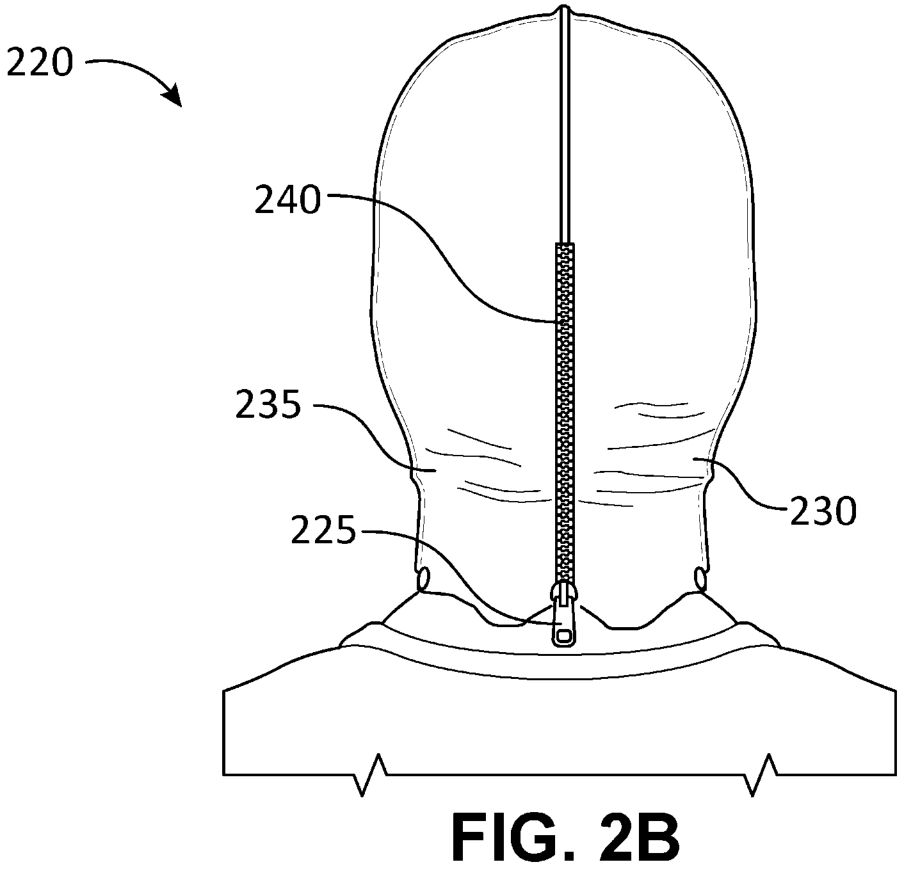
FIG. 2B depicts an exemplary thermal compressive mask zipper embodiment.

FIG. 2B depicts an exemplary thermal compressive mask zipper embodiment 220. The embodiment 220 includes a mask having a zipper 225. The zipper 225 extends along a central posterior axis and is configured to join a left side 235 and a right side 230 of the mask. A seam 240 represents the junction where the opposing sides of the mask meet along the zipper 225 when fastened. This seam 240 provides structural continuity across the rear of the head and neck, helping to preserve uniform compression and mask alignment during use. The zipper facilitates convenient donning and doffing while maintaining the integrity of the compressive fit. Additionally, this rear opening helps mitigate shearing forces on facial flaps during early postoperative healing, which is particularly important in surgeries involving delicate skin reconstruction.

Figure 3:
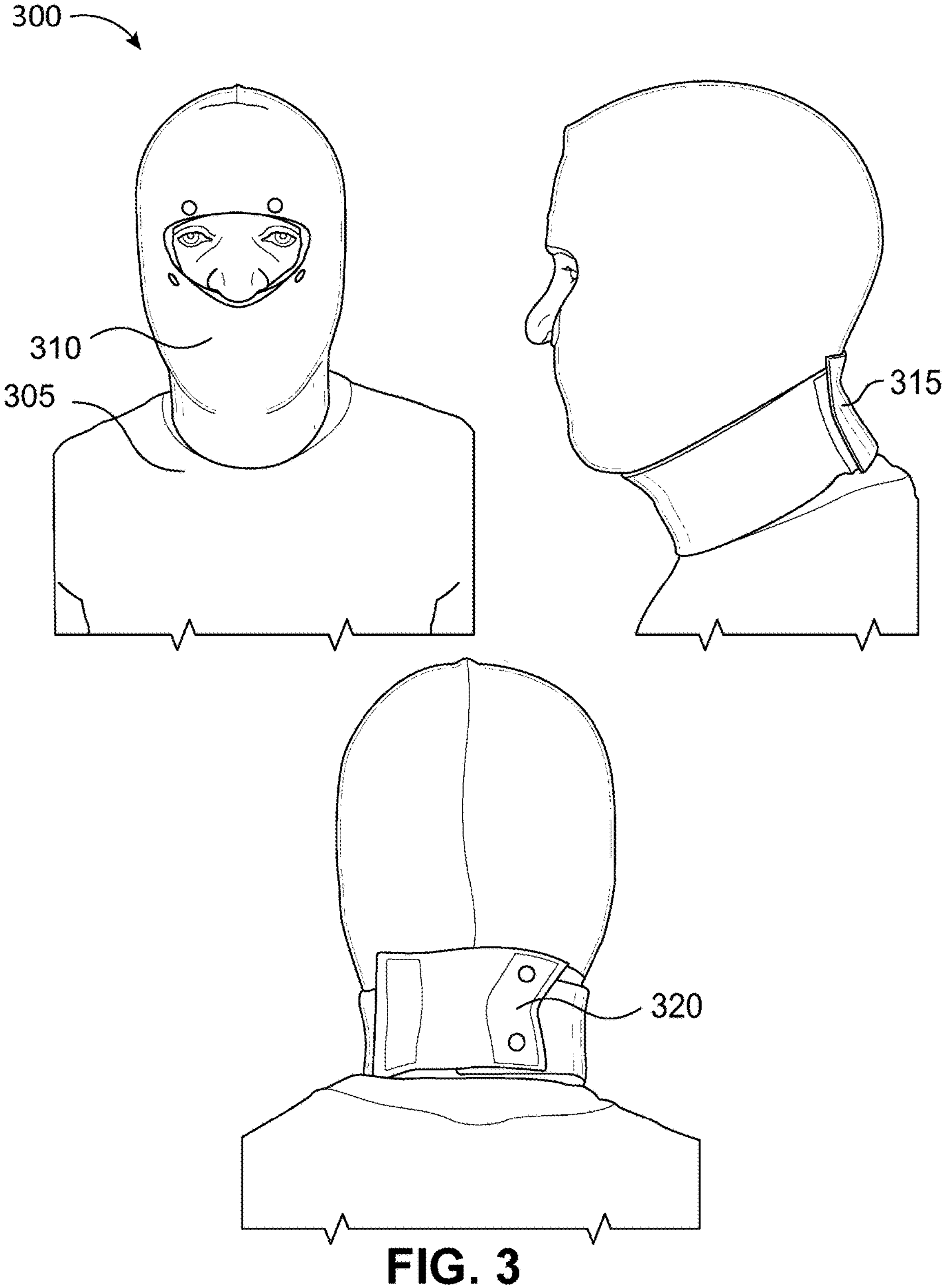
FIG. 3 depicts an exemplary neck strap embodiment.

FIG. 3 depicts various views of an exemplary neck strap embodiment 300. A patient 305 is wearing the embodiment 300. A thermal-compressive surgical-treatment mask 310 is secured to the patient 305. The thermal-compressive surgical-treatment mask includes a decouplable neck strap 315. The neck strap 315 wraps around the anterior and posterior cervical regions and is fastened using a fastener 320. The fastener 320 may include snaps, Velcro, or magnetic fasteners that allow the strap to be tensioned to apply targeted compression to the neck. This embodiment may facilitate lymphatic drainage from the craniofacial region by extending pressure gradients into the cervical lymphatic zones.

Some embodiments, may, for example, include a facemask embodiment that includes a rear stitching. The rear stitching may, for example, enhance the mask's structural integrity and ensure a snug fit around the contours of the head. This embodiment may, for example, prevent slippage during wear. This embodiment may, for example, contribute to the uniform distribution of compressive forces, maximizing therapeutic efficacy.

Figure 4:
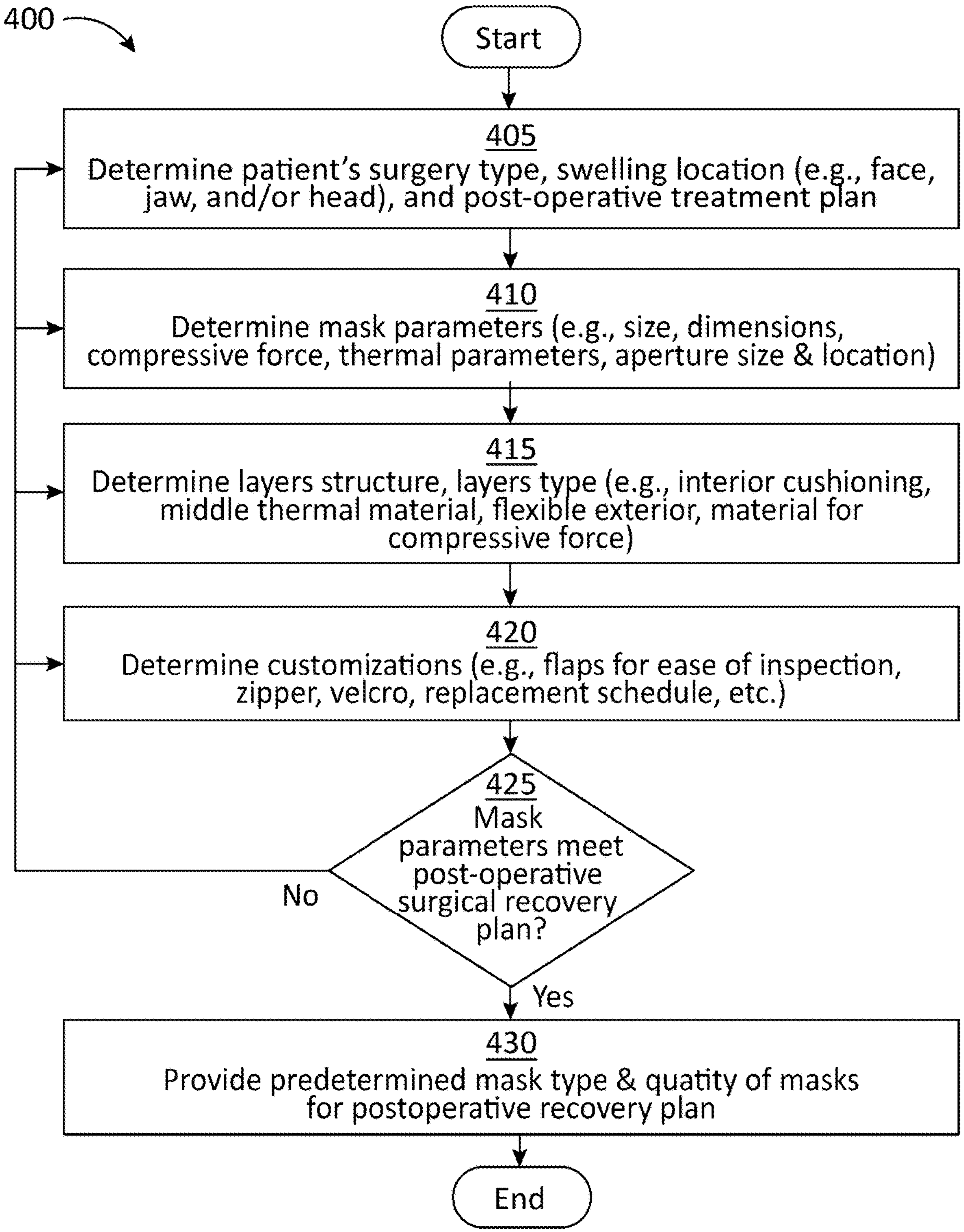
FIG. 4 is a flowchart illustrating an exemplary method of determining a mask type for a user based on their type of surgery.

FIG. 4 depicts a flowchart illustrating an exemplary method 400 of determining a compressive facemask to treat a user's swelling post-surgery. The exemplary method 400 includes in step 405 a user of the method determining the patient's surgery type, swelling location, e.g., on face, jaw, head, and a post operative treatment plan. The user of the method may, for example, include a healthcare provider. The user of the method may, for example, include a patient under a doctor's guidance. The user of the method may, for example, use the method as an evaluation process in selecting a post-operative surgical recovery plan. Step 405 may, for example, include determining the specific type of surgery to determine the swelling locations that need to be addressed. Identifying the surgery type and swelling locations may, for example, enable the customization of the mask to target those areas effectively. A doctor during this step may, for example, use the method to craft a tailored post-operative treatment plan that incorporates the use of the thermal-compressive mask. This plan may, for example, be devised based on the surgery's nature and the patient's individual recovery needs. The plan may, for example, ensure that the mask's application is optimized to expedite healing, reduce swelling, and minimize discomfort.

In step 410, a user of the method determines the mask parameters e.g., size, dimension, compressive force, thermal parameters, aperture size, and aperture location. The compressive force exerted by the mask may, for example, be calibrated to optimize swelling reduction and enhance circulation without compromising patient comfort. Thermal parameters may, for example, be established, including the desired temperature range and duration of application, tailored to the nature of the surgery and the patient's specific recovery needs. The size and location of the aperture may, for example, be selected to accommodate the patient's facial features, ensuring unobstructed breathing and access to post-surgical treatment sites. This comprehensive evaluation of mask parameters may, for example, advantageously ensure that the mask fits the anatomical and therapeutic requirements of the patient. The evaluation of the mask may, for example, be used to make sure the mask's parameters align with the overarching goals of the post-operative treatment plan, facilitating a smoother and more comfortable recovery process.

In step 415, a user of the method determines the layer structure. The layer structure may, for example, include interior cushioning. The layer structure may, for example, include a middle thermal material section. The layer structure may, for example, include an exterior that includes a flexible compressive force structure. The user of the method may, for example, delves into an intricate process of determining the mask's layer structure. The user of the method may, for example, carefully consider and construct the mask's composition, starting with the interior layer, which involves selecting a suitable cushioning material. This interior cushioning may, for example, provide comfort and ensure the mask's snug fit against the sensitive post-operative skin, reducing the risk of irritation. The user of the method may, for example, focus on the middle layer, where a thermal material section is integrated. This layer may, for example, maintain the desired temperature—be it warm or cold—thereby aiding in the reduction of swelling and the acceleration of the healing process through controlled thermal therapy. Finally, the exterior layer of the mask may, for example, be designed to encompass a flexible yet durable material capable of applying a uniform compressive force. This external structure may, for example, support the mask's overall integrity but also enhances the compressive therapy's effectiveness by evenly distributing pressure across the treatment area. Together, these layers may, for example, form a synergistic structure that optimizes the mask's functionality, making it a comprehensive solution for post-operative recovery.

In step 420, a user of the method may, for example, refine the mask through customizations that cater to the unique needs of the patient and the specifics of the post-operative recovery process. The user of the method may, for example, enhance the mask's functionality and user experience. For instance, a user of the method may, for example, include flaps on the mask. The flaps may, for example, be considered for ease of inspection, allowing healthcare providers or patients themselves to check on the healing progress without fully removing the mask, thereby maintaining therapeutic conditions while enabling regular monitoring. Additionally, a user of the method may, for example, consider the integration of a zipper into the mask's design to facilitate easy application and removal, ensuring that the mask can be comfortably fitted and adjusted without disturbing sensitive post-surgical areas. Velcro attachments are another customization under consideration, offering a versatile and adjustable closure mechanism that can accommodate swelling fluctuations and ensure a snug fit throughout the recovery period. Furthermore, establishing a replacement schedule for the mask may, for example, be important for a post-recovery plan prescribed by a doctor. The schedule may, for example, ensure that the mask remains effective and hygienic over the course of its use. This step of determining customizations may, for example, be important in creating a mask that is therapeutic, practical, and user-friendly, and tailored to meet the diverse requirements of post-surgical care.

In step 425, a user of the method determines whether the mask parameters meet the post-operative surgical recovery plan. If the user of the method determines that the mask meets the parameters, they may proceed to step 430. In step 430, a user of the method provides the predetermined mask type to the patient and a quantity of masks sufficient for the post operative recovery plan. If the user of the method determines that mask does not meet all the requirements necessary for the recovery plan, the user of the method may, for example, proceed to step 410, 415, and/or 420.

Figure 5:
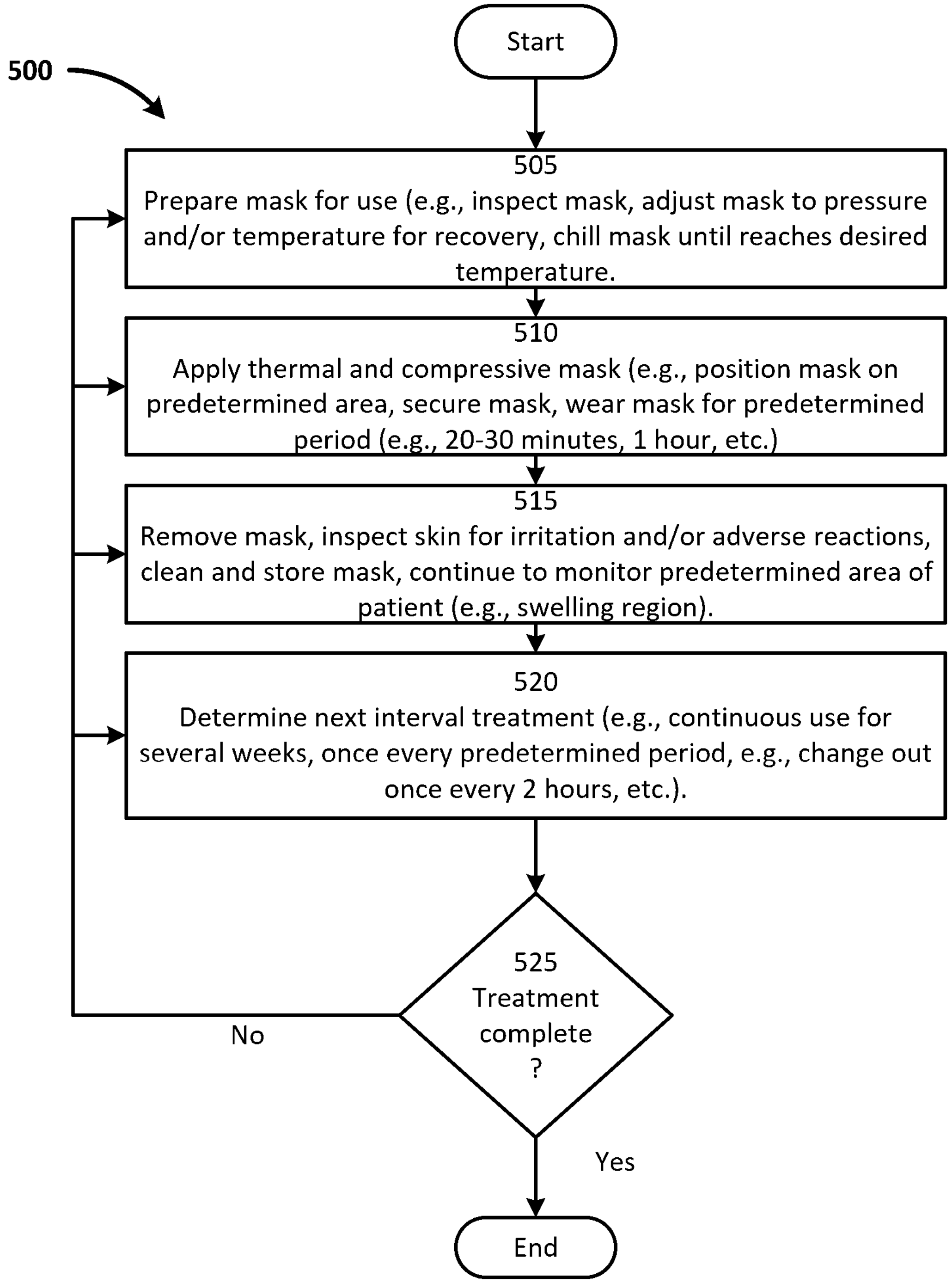
FIG. 5 depicts a flowchart illustrating an exemplary method of determining a compressive facemask to treat a user's swelling post-surgery.
Figure 6:
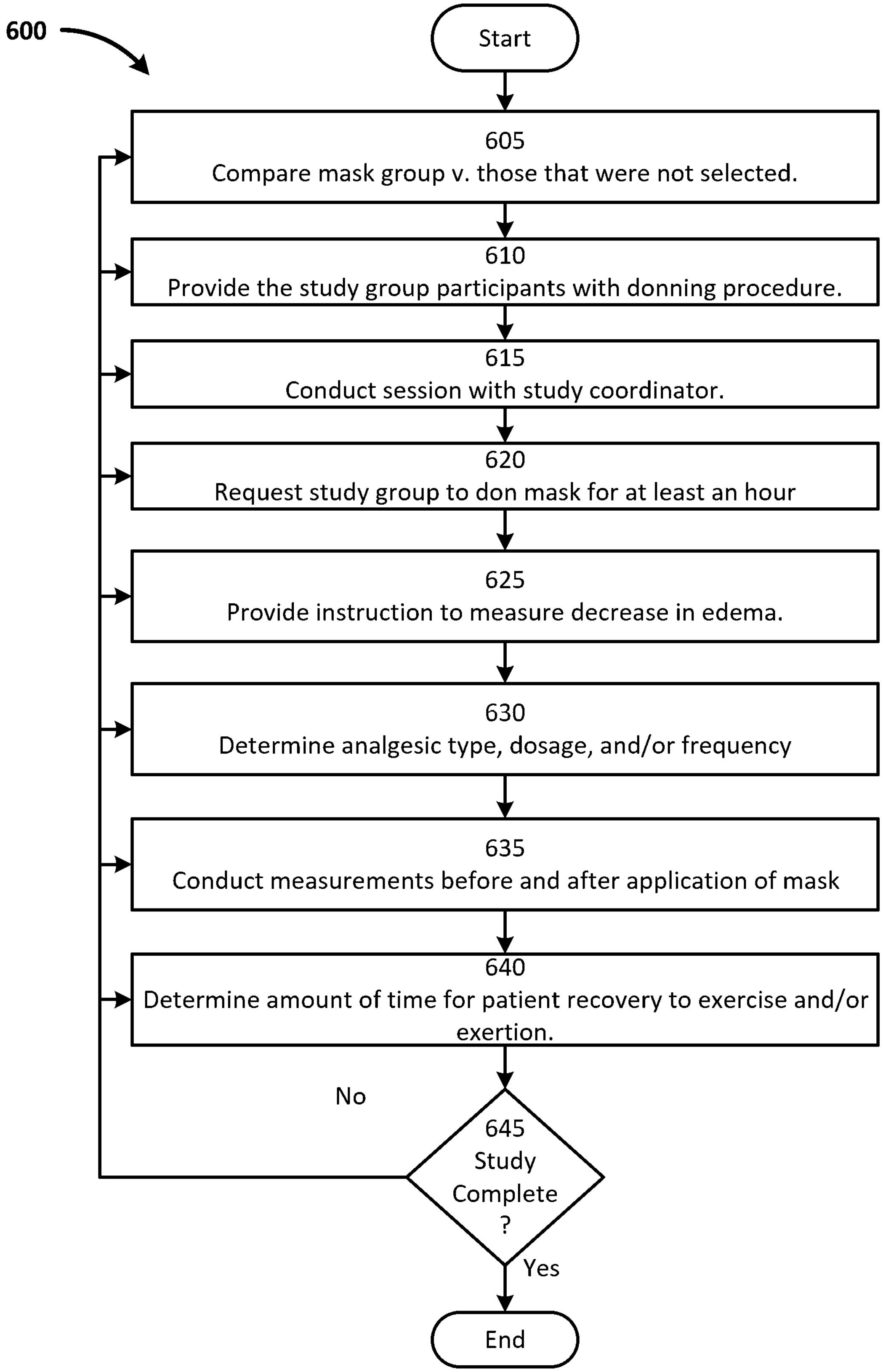
FIG. 6 depicts a flowchart illustrating an exemplary method used in a material and patient selection study.

FIG. 5 depicts a flowchart illustrating an exemplary method 500 of using a compressive facemask to treat a user's swelling post-surgery. In step 505, a user of the method prepares the mask for use. The process begins with a thorough inspection of the mask to check for any damage or irregularities that could affect its performance or cause discomfort to the patient. Following the inspection, the mask may, for example, be adjusted to the appropriate pressure and temperature settings, tailored to the specific needs of the patient's recovery plan. For example, if cooling therapy is indicated, the mask may, for example, be chilled until it reaches the desired temperature. This preparatory step may, for example, be used for optimal therapeutic use, ensuring that it is ready to provide the necessary thermal and compressive support to the affected area.

In step 510, a user of the method applies the thermal and compressive mask. The mask may, for example, be positioned over the predetermined area, ensuring full coverage of the targeted surgical site. Once in place, the mask is secured using the built-in mechanisms, such as Velcro straps, and/or zippers, to ensure it remains snug and effective throughout the therapy session. The patient is then instructed to wear the mask for a predetermined period, which could range from a short session of 20-30 minutes to longer durations of up to an hour, depending on the recovery requirements and the healthcare provider's recommendations. This step may, for example, help reduce swelling and pain relief of the patient post-surgery.

In step 515, a user of the method following the therapy session, may, for example, carefully remove the mask to inspect the skin underneath for any signs of irritation or adverse reactions. This inspection may, for example, be used to assess the skin's response to the treatment and make any necessary adjustments to the therapy regimen. After the inspection, the mask is cleaned according to the manufacturer's instructions and stored properly to maintain its hygiene and functionality for future use. The area of the patient that was under treatment may, for example, be continuously monitored, particularly for changes in swelling, to gauge the effectiveness of the therapy and determine if adjustments are needed in subsequent sessions.

A user of the method in step 520 may, for example, determine the next interval for treatment. The user of the method may, for example, strategically determine the recovery plan based on the patient's progress and the specific requirements of their post-operative care. The frequency and duration of mask use may, for example, be adjusted. The mask treatment may, for example, involve continuous use for several weeks and/or application once every predetermined period, such as every two hours. This interval may, for example, be determined with the goal of optimizing recovery, managing pain, and reducing swelling effectively, considering the patient's comfort and the healing trajectory observed thus far.

In step 525, a user of the method determines if the treatment is complete. The completion of treatment may, for example, mark a milestone in the patient's recovery journey. This final stage may, for example, be reached after a series of successful therapy sessions with the thermal and compressive mask, following the carefully planned treatment intervals. The decision to conclude the treatment may, for example, be based on the healthcare provider's assessment that the patient has achieved the desired outcomes, such as reduced swelling and pain, and that the surgical site has healed sufficiently. At this point, the focus may, for example, shift to other aspects of recovery or maintenance, marking the end of this therapeutic intervention but continuing the overall journey towards complete healing. If the healing process is not complete, a user of the method may, for example, proceed to step 505, 510, 515, and/or 520 to continue to treat the post-operative surgical location.

In some embodiments, the thermal compressive mask may, for example, be configured to test the potential benefit of regular and or routine use of the thermal decompression mask, following various operations on the head and neck.

The thermal compressive mask may, for example, be used in a material and patient selection method 600. In step 605, a user of the method may, for example, compare groups that wear the mask as instructed, versus those that were not selected, or did not want to art participate in the study. In step 610, a user of the method may, for example, provide the study group participants with a video with important information, including freezing mask for at least one hour prior to donning; for donning and doffing the decompression mask. In step 615, a user of the method may, for example, have at least one session with a study coordinator to ensure proper donning of the mask. In step 620, a user of the method may, for example, request that the study group to don at least one time for one hour, to see if they are willing to proceed with the study. In step 625, in video for example, a user of the method may provide instructions to measure the decrease in edema of the face at the neck level. For context, Edema is a medical condition characterized by the accumulation of excess fluid in the body's tissues, leading to swelling, often observed in the legs, feet, arms, or hands. Measuring edema in a patient may, for example, include involves assessing the extent of swelling through physical examination, measuring limb circumference, evaluating changes in body weight, and utilizing imaging techniques like ultrasound or MRI to quantify fluid accumulation.

In step 625, a user of the method may, for example, ask the patients to monitor the change in conditions. In steps 630, a user of the method may, for example, determine the analgesic type, dose, and frequency.

Figure 7:
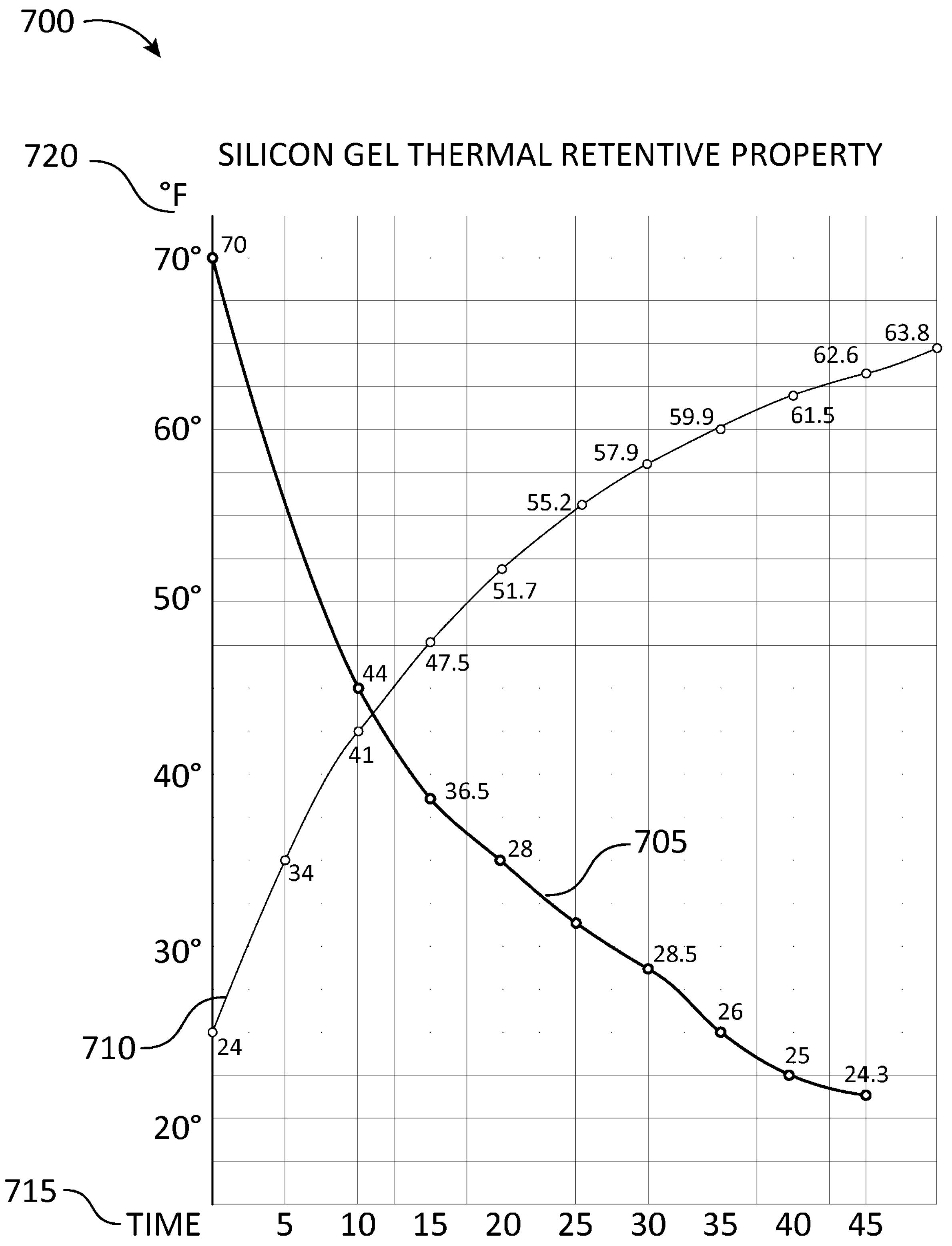
FIG. 7 depicts an exemplary graph depicting the silicone gel thermal retentive property.

FIG. 7 depicts an exemplary graph 700 depicting the silicone gel thermal retentive property. The graph 700 includes a vertical axis 720 representing temperature in degrees Fahrenheit (° F.). The graph 700 includes a horizontal axis 715 representing time in minutes. The temperature-time cooling curve 705 illustrates the thermal behavior of the silicone-based gel layer over a 45-minute duration following pre-conditioning. The cooling curve 705 begins at approximately 70° F., but drops to about 24° F. over the full 45-minute observation period. The graph includes a warming curve 710 where the temperature gradually rises back to approximately 63.8° F. by the end of 45 minutes. It should be noted that this cooling curve was generated without a mask applied to a patient's skin, and thermal dissipation may vary when in contact with warm tissue. Nonetheless, the thermal profile confirms the gel's ability to retain cold within a therapeutically useful range.

In some embodiments, the silicone-based gel layer may be pre-conditioned using standard refrigeration or freezer storage to reach a target temperature prior to use. The gel's high thermal mass and low thermal conductivity may slow the transfer of heat from the ambient environment, allowing the mask to remain cool throughout a full treatment session. In certain configurations, the gel layer may be enclosed by an insulating outer textile—such as neoprene or multilayer elastic fabric—to further reduce thermal gain during wear. Some embodiments may include thermochromic indicators on the mask surface to visually signal readiness for use or loss of effective cooling. This passive cooling approach may enable the mask to be worn comfortably for up to 30 minutes without requiring external tubing, active refrigeration, or replacement ice packs, improving convenience and patient compliance during at-home or in-clinic therapy.

In some embodiments, a temperature-swapping protocol may be implemented wherein two or more masks are alternated in 30-minute intervals to maintain continuous cooling and compressive therapy. For example, while one mask is in use, a second mask may be reconditioning in a refrigeration or freezer unit. This swap cycle may allow for sustained cold application over extended periods without thermal performance degradation. When combined with the graduated compression structure of the mask, repeated temperature-controlled sessions may reduce post-operative swelling more effectively than cold therapy or compression alone. The integration of both cooling and compression across lymphatic drainage zones may, for example, promote more efficient fluid clearance, minimize inflammation, and decrease reliance on pharmacologic pain management. Some embodiments may support recovery protocols where masks are worn multiple times per day, with temperature cycling and compressive fit contributing to faster wound healing and improved patient outcomes.

For context, the analgesic type may, for example, delineate the classification of pain relief medications or treatments, ranging from nonsteroidal anti-inflammatory drugs (NSAIDs), including COX-2 inhibitors, and acetaminophen to opioids and adjuvant analgesics. Each is designed with specific targets and mechanisms to alleviate pain. COX-2 inhibitors, being a subclass of NSAIDs, are listed here immediately after NSAIDs to reflect their pharmacological relationship.

In step 635, a user of the method may, for example, conduct measurements of patients swelling before and after donning. A user of the method may, for example, determine the amount of time to sleeping flat (e.g., without an incline). In step 640, a user of the method may, for example, determine the amount of time to exercise and/or exertion.

The user of the method may, for example, take objective scores such as the frequency of seroma aspirations. The user of the method may, for example, take feedback from the postoperative patient's phone calls, emails, or texts to the physician's office with problems.

Conductors of the study and/or physicians may, for example, look for postoperative complications, including seroma, hematoma, infections, skin, necrosis, hypertrophic scar. In step 645 A user of the method may, for example, create studies and report the results of various measurements as listed above. A user of the method may, for example, collect information to form a comparison of analgesic dosage, time to sleeping, flat, subjective sense of satisfaction, scores, and postoperative complications. In some embodiment of the study, with enough masks, a user of the method may, for example, create a multi-institutional study as a prospective trial, or even comparing them against historical controls, or those that opted not to enroll. The user of the method may, for example, ensure to maximize the chance for 100% compliance in the study group. The patient may, for example, purchase the mask ahead of time as a part of the qualification and preparatory video. In some embodiments, the mask study may, for example, be part of an enhanced recovery after surgery (ERAS) program.

In some embodiments, the mask may, for example, be applied first followed by a user. A second person may, for example, assist a user put on the mask. The mask may, for example, mold a user. The mask may, for example, have to a predetermined amount of tightness to be comfortable.

In some embodiments, the mask may, for example, include a pressure gradient. The pressure gradient may, for example, allow for variable compressive forces across different sections of the mask, delivering stronger compression to areas requiring substantial support for swelling reduction and gentler pressure to more delicate regions to prevent discomfort or compromised circulation. A variation in compression may, for example, be achieved through the careful selection and structuring of materials, ensuring that each area of the mask applies the appropriate level of pressure for optimal healing benefits while maintaining patient comfort. Such a design element underscores the mask's advanced therapeutic approach, catering to the nuanced needs of post-surgical recovery by offering a tailored, effective solution for managing swelling, promoting blood flow, and ensuring a more comfortable healing process.

Although various embodiments have been described with reference to the figures, other embodiments are possible.

Although an exemplary system has been described with reference to FIGS. 1-7, other implementations may be deployed in other industrial, scientific, medical, commercial, and/or residential applications.

In industrial contexts, the thermal compressive pressure gradient mask may, for example, be used in the manufacturing of medical devices and protective gear. Industries focused on creating innovative health and safety products can leverage this technology to produce masks designed for workers in environments that require facial protection from extreme temperatures and pressures. For instance, in chemical manufacturing or metallurgy, where exposure to heat and harmful substances is common, such masks could offer both thermal protection and facial compression, reducing the risk of thermal burns and aiding in the prevention of swelling or injuries caused by exposure to hazardous conditions.

In scientific research, particularly within biomedical and ergonomic studies, the mask's unique combination of thermal control and compressive pressure offers a tool for investigating the effects of these variables on human tissue and vascular health. Scientists could use the mask in clinical trials to study its efficacy in promoting venous and lymphatic drainage, understanding the role of thermal and pressure therapies in healing and recovery. Unlike some compressive devices that use latex, this system is latex-free and therefore safe for patients with latex allergies, broadening its clinical usability.

Medically, the thermal-compressive surgical-treatment mask may, for example, be used in postoperative care, particularly for patients undergoing facial, thyroid, jaw, and/or head surgeries. The design of the mask accommodates various face and skull structures while providing adjustable thermal and pressure therapies, makes it an essential tool for managing pain, swelling, and promoting lymphatic drainage post-surgery. This mask could be particularly beneficial in plastic surgery and maxillofacial surgical settings, where precision in postoperative care can greatly influence healing outcomes and patient comfort. By mitigating pain and reducing swelling through controlled thermal and compressive interventions, the mask aids in quicker, more comfortable recovery periods for patients.

Commercially, this mask may, for example, offer a method of pain and swelling management. The masks adaptability to different facial structures, combined with the capability to provide consistent thermal therapy and compression, makes it an attractive product for pharmacies, medical supply stores, and online health care retailers. Additionally, the mask's innovative design could appeal to cosmetic surgery clinics and dental offices as a value-added service to offer patients, enhancing patient satisfaction and care outcomes. The commercial success of such a product would depend on effective marketing strategies highlighting its benefits over traditional postoperative care methods.

For individuals recovering from surgeries at home, the thermal compressive pressure gradient mask offers a practical and effective means of managing postoperative recovery, especially in the critical initial days following surgery. The mask may, for example, allow a user to use the product with ease. The mask may, for example, allow a user to maintain a certain temperature and provide targeted pressure. The mask may, for example, allow a user a more comfortable recovery by minimizing reliance on medication for pain and swelling management. Additionally, for those undergoing cosmetic procedures or minor surgeries that do not require hospital stays, this mask may, for example, enhance the comfort and efficiency of home recovery. The facemask may, for example, be an item in home healthcare kits (e.g., for burn related injuries).

In some embodiments, a detachable neck strap may, for example, be configured to couple with the main facial mask via a receiving and opposing coupling mechanism. The neck strap may, for example, provide graduated compression along the cervical region to complement craniofacial compression and maintain confluent pressure gradients. Such a configuration may, for example, reduce edema in post-surgical patients by facilitating lymphatic drainage from the head into the cervical lymphatic system. The neck strap may, for example, be used independently or in conjunction with the facial component, especially in surgeries localized to the neck such as thyroidectomy, carotid endarterectomy, or lymphadenectomy. The neck strap may, for example, include similar multilayer construction as the main mask, including an inner cushioning fabric, silicone gel layer, and an exterior elastic compressive layer. This modular design may, for example, allow for targeted thermal-compression therapy adaptable to patient-specific anatomical or surgical needs.

In some embodiments, the inner silicone gel layer may, for example, be constructed from a clear, medical-grade silicone selected for its viscoelastic properties and thermal retention characteristics. This silicone layer may, for example, be non-adherent to the skin to prevent irritation, allowing for extended wear post-operatively without causing dermatologic complications. The gel may, for example, distribute pressure evenly across complex craniofacial surfaces while maintaining localized cooling or heating for extended durations. The silicone's formulation may, for example, meet biocompatibility standards for prolonged dermal contact in medical devices. The material may, for example, be derived from scar therapy sheet technology but used here in a non-wound-contacting layered configuration to assist with swelling and pain. Additionally, this silicone gel may, for example, serve to thermally insulate the inner layers from external temperature variation during storage or patient wear.

In some embodiments, the inner silicone gel layer may, for example, be constructed from a clear, medical-grade silicone selected for its viscoelastic properties and thermal retention characteristics. This silicone layer may, for example, be adherent rather than non-adherent, allowing it to conform closely and stay in contact with the treatment area. The silicone layer may, for example, be used in wound care to promote healing, and its tackiness ensures continued contact for improved therapeutic outcomes. The gel may, for example, distribute pressure evenly across complex craniofacial surfaces while maintaining localized cooling or heating for extended durations.

In some embodiments, the thermal-compressive surgical mask may, for example, be shaped to deliver non-uniform pressure across the treatment area in accordance with lymphatic drainage pathways. In some embodiments, pressure may, for example, be greatest over the scalp and periorbital regions and diminish toward the jawline and neck to avoid venous stasis. The pattern of compression may, for example, be achieved through geometric contouring of the mask combined with the elastic gradient of the exterior material. This graduated design may, for example, enhance fluid mobilization from the superficial venous system into deeper drainage basins, thereby reducing swelling. The compressive mask may, for example, be shaped to avoid pressure-sensitive anatomical landmarks such as the trachea, carotid bifurcation, and auricular cartilage. In some embodiments, internal pressure mapping during prototyping may, for example, inform layer density or stitch reinforcement patterns to achieve desired gradients.

In some embodiments, the thermal-compressive surgical-treatment system may, for example, be adapted for use across a variety of craniofacial and cervical surgical procedures. For maxillofacial and orthognathic surgeries, such as mandibular advancement or dental extractions, the system may, for example, include adjustable apertures or contoured gel zones that conform to jaw structures without impeding occlusion or intermaxillary fixation. In cases of thyroidectomy, parathyroidectomy, carotid endarterectomy, or lymph node dissection, the attachable neck strap may, for example, provide localized compression to facilitate lymphatic and venous drainage in the cervical region. Additionally, the device may, for example, be utilized for patients recovering from ENT procedures such as parotidectomy, rhinoplasty, or mastoidectomy, with pressure zones modified to avoid surgical sites while still delivering therapeutic effect. The system may, for example, be configured as a modular, customizable assembly adaptable to the specific anatomical and clinical requirements of a given surgical procedure.

In some embodiments, the system may, for example, be configured for targeted use following thyroidectomy, parathyroidectomy, or other anterior cervical surgeries. The attachable neck strap may, for example, deliver localized graduated compression across the anterior neck region to minimize postoperative edema and support lymphatic clearance. The strap may, for example, conform anatomically to avoid undue pressure over the trachea and carotid sheath, while still maintaining sufficient compressive force for therapeutic benefit. The strap's multilayer construction may, for example, include a thermally active gel core and stretchable outer compression fabric to provide both cooling and mechanical support. The device may, for example, be used independently from the facial component for surgeries localized to the cervical region. Such configurations may, for example, benefit patients recovering from thyroid-related procedures where targeted edema reduction and comfort are critical to healing outcomes.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A therapeutic chilling multi-layered silicone mask comprising:

a silicone-based gel layer and an aperture configured to fit around an airways of a patient;

a detachable neck strap comprising a coupling member coupled to a multi-layered mask configured such that the detachable neck strap is operably secured;

a thermal-compressive interface extending across a predetermined medical region, the thermal-compressive interface comprising a graduated compression structure formed by the multi-layered mask comprising an inner liner layer, the silicone-based gel layer, and an outer elastic fabric layer configured to conform to anatomical contours and maintain targeted thermal and compressive contact across the predetermined medical region; and, wherein the graduated compression structure is configured to vary pressure distribution across the multi-layered mask configured to a predefined profile aligned with lymphatic drainage pathways, wherein the graduated compression structure is configured to vary pressure distribution across the multi-layered mask such that the multi-layered mask is configured to apply higher pressure to regions near the scalp and jawline and lower pressure near healing areas, and, wherein, the multi-layered mask is configured to apply cold and graduated compression to reduce pain and swelling and enhance lymphatic and venous drainage for a patient post-surgery.

2. The therapeutic chilling multi-layered silicone mask of claim 1, wherein the outer elastic fabric layer comprises a neoprene-based textile.

3. The therapeutic chilling multi-layered silicone mask of claim 1, wherein the inner liner layer is formed of a microfiber textile configured to wick moisture away from a skin surface of the patient.

4. The therapeutic chilling multi-layered silicone mask of claim 1, wherein the inner liner layer is releasably couplable to the silicone-based gel layer using a hook-and-loop or adhesive interface.

5. The therapeutic chilling multi-layered silicone mask of claim 1, further comprising a lace-tightening system located along a posterior portion of the multi-layered mask and configured to adjust compressive force across a head region.

6. The therapeutic chilling multi-layered silicone mask of claim 5, wherein the lace-tightening system comprises a cord routed through a series of grommets positioned longitudinally on a rear of the multi-layered mask.

7. The therapeutic chilling multi-layered silicone mask of claim 1, further comprising a zipper positioned along a central posterior axis of the multi-layered mask.

8. The therapeutic chilling multi-layered silicone mask of claim 1, wherein the detachable neck strap comprises a curved cutout configured to contour to a submandibular region and a submental region of the patient.

9. The therapeutic chilling multi-layered silicone mask of claim 1, wherein the multi-layered mask comprises a posterior seam extending from a frontal scalp region to a nape of the patient.

10. The therapeutic chilling multi-layered silicone mask of claim 1, wherein a neck portion includes a narrowed section to retain the multi-layered mask below a chin of the patient.

11. The therapeutic chilling multi-layered silicone mask of claim 1, wherein the multi-layered mask is unitarily constructed.

12. The therapeutic chilling multi-layered silicone mask of claim 1, wherein the inner liner layer comprises an anatomical shaping around a face of the patient.

13. The therapeutic chilling multi-layered silicone mask of claim 1, wherein the multi-layered mask includes a receiving coupling device configured to operatively couple detachable neck strap.

14. The therapeutic chilling multi-layered silicone mask of claim 1, wherein the multi-layered mask is reusable and configured for repeated chilling cycles without degradation of structural integrity.

15. The therapeutic chilling multi-layered silicone mask of claim 1, wherein the multi-layered mask is configured to be donned and removed without assistance.

* * * * *